United States Patent [19]

Hitch

[11] 4,137,772

[45] Feb. 6, 1979

[54] AUTOMATED MEANS FOR HIGH VOLUME, DISCRETE DEPTH PLANKTON COLLECTING

[76] Inventor: Robert K. Hitch, 1769 Willard St. NW., Washington, D.C. 20009

[21] Appl. No.: 805,593

[22] Filed: Jun. 13, 1977

[51] Int. Cl.² .............................................. G01N 1/14
[52] U.S. Cl. .................................. 73/421 R; 73/425.2
[58] Field of Search .............. 73/421 R, 170 A, 425.2; 43/4

[56] References Cited

U.S. PATENT DOCUMENTS

| 2,672,987 | 3/1954 | Hutchinson | 73/421 R |
| 3,466,782 | 9/1969 | Stuart | 73/421 R |

OTHER PUBLICATIONS

W. J. Whitfield, AEC-NASA Tech. Brief, #68-10231, Jul. 1968.

Primary Examiner—Anthony V. Ciarlante

[57] ABSTRACT

A plankton collector comprised of an open cylinder having a netting and motor with an attached propeller. The motorized propeller and netting are attached within the cylinder so that the propeller pulls water through the netting thereby concentrating the planktonic organisms. Flowmeters can easily be attached for quanitative measurement of the water flow. Two species of this invention are set forth. One species is designed to be tethered by its electrical cord in flowing water. The other species, has a portable power supply and is designed to be used by a submerged diver.

1 Claim, 4 Drawing Figures

AUTOMATED MEANS FOR HIGH VOLUME, DISCRETE DEPTH PLANKTON COLLECTING

This invention relates to the art of collecting plankton samples. A principal object of the present invention is to provide an improved and simplified plankton sampling means.

Accordingly, it is an object of the present invention to overcome certain disadvantages associated with the plankton sampling devices now in use. Principal forms of plankton collectors now in use include the submersible centrifugal pump with a hose leading to a collecting net at the surface and the plankton tow net pulled by a boat. The centrifugal pump is awkward to use and inefficient in that much energy is lost in friction within the hoses to the surface. The amount of water sampled when using the centrifugal pump technique is difficult to quantify and the hoses to the surface are subject to clogging. Further, the vacuum created by the centrifugal pump intake often causes these devices to rotate in the water and to entangle the support ropes and cables. The most serious drawback to the pump technique is its tendency to mutilate planktonic specimens in the pump impellers. The boat-towed net technique requires considerable expenditures of personnel and equipment and sampling a discrete water stratum is difficult by this means.

With the foregoing objects in view, as will become apparent from the following specification, this invention resides in the placement of a motorized propeller inside of cylindrical housing, open at both ends so that the propeller draws water through a plankton-filtering net which is also mounted within the housing.

In the first species utilizing this invention, a flowmeter, the net, and the motorized propeller are mounted in three, easily separable sections or stages. The separable sections allow the operator quick access to the net, flowmeter, propeller and motor. This first species is lowered from the surface to the desired sampling depth on a support cable which encloses the electrical conductors leading to the motor. Before the collector is turned off and raised to the surface a closing device can be lowered from the surface by the operator for discrete depth sampling.

The second species of this invention utilizes a portable power supply. Handholds and arm supports are mounted to the outside of the housing so it can be steered by a diver as he is pulled through the water by the thrust of the motorized propeller. This species can be used in lotic or limnetic aquatic systems. Because the device constantly pulls the diver forward, recirculation of previously filtered water is kept to a minimum.

Figure 1:
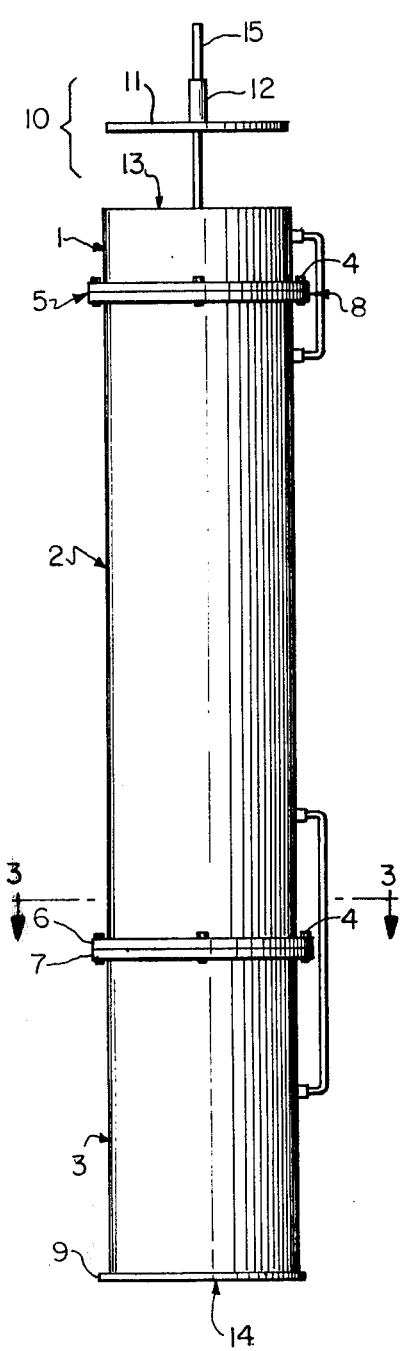
FIG. 1 is an elevation view of the first species of plankton collector shown with the closing device about to seal the intake.
Figure 2:
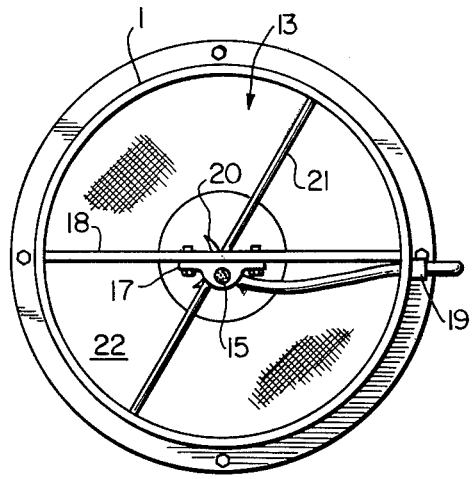
FIG. 2 is a plan view of the first stage of the first species of plankton collector.
Figure 3:
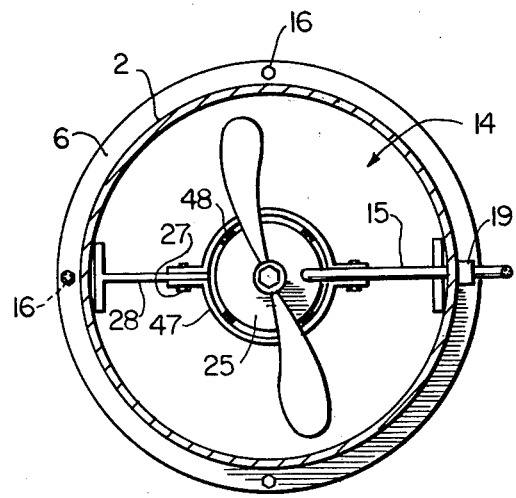
FIG. 3 is a plan view of the third stage of the first species of plankton collector.
Figure 4:
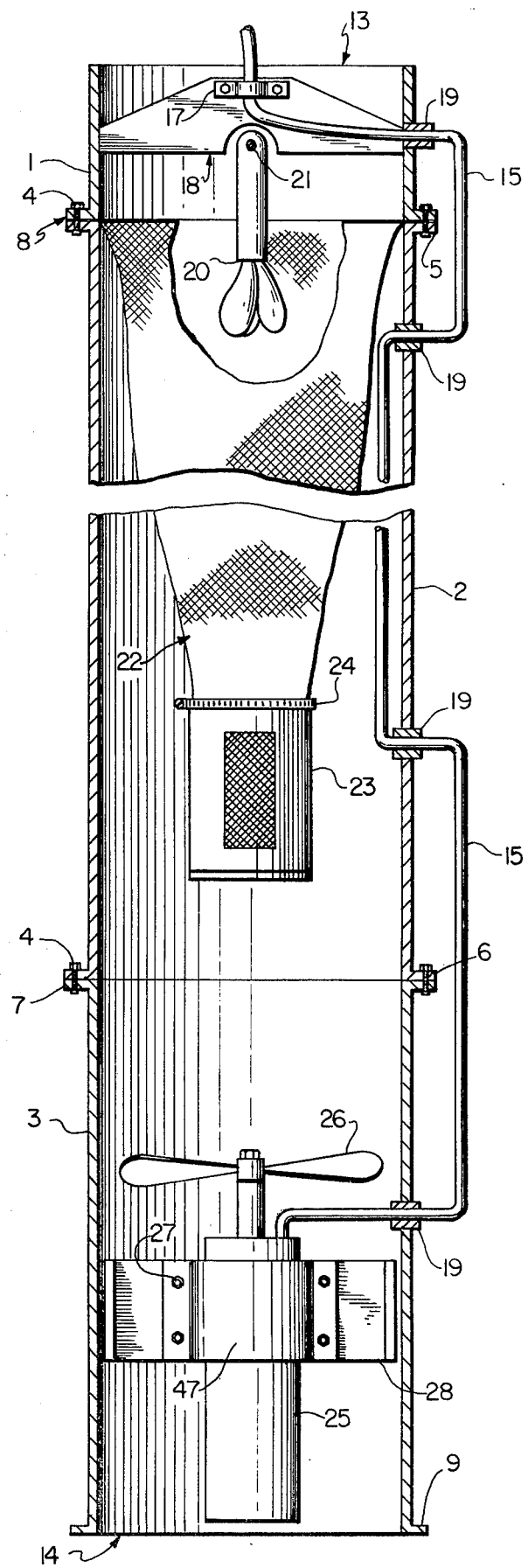
FIG. 4 is an elevation in section view of FIG. 1 without the closing device.

Referring to the drawings which show an elevation view of the first species of plankton collector the three stages are designated 1, 2, and 3. Each stage is a hollow cylinder attached to the adjoining cylinder by the flange bolts (4). Four equally-spaced flange bolt holes (16) are threaded in the second stage top flange (5) and the third stage top flange (7) for securing the flange bolts once they are inserted through the unthreaded holes of the first stage flange (8) and the second stage bottom flange (6). The third stage bottom flange (9) reinforces the bottom of the third stage when the apparatus is in a standing position. The cylindrical stages could be made of any relatively inflexible corrosion resistant material. In the experimental forms produced by the applicant, the material selected was aluminum.

The closing device (10) is comprised of a heavy disc (11), slightly larger in diameter than the intake (13) with a central guide hole, around the rim of which is perpendicularly attached a short, open tube (12) which maintains the disc in a horizontal position on the electric power and support cable (15). The electric power and support cable is mounted to the collector by the cable brace (17) which is in turn belted to the cable support strut (18).

When deploying the first species of plankton collector, the operator lowers the same into the water on the electric power and support cable (15) keeping the closing device (10) behind. The operator, then, turns on the electric power at the surface activating the propeller and starting the flow of water into the intake (13) and out through the exhaust (14). Planktonic creatures have been filtered out of this exhausted water by the plankton netting in the net (22) and plankton bucket (23). After the appropriate sampling period, the operator releases the closing device (10) to seal the intake. The power is then turned off and the collector is raised to the surface by the electric power and support cable (15). The collector is preferably stood on the third stage bottom flange (9) and the closing device (10) is slid up the electric power and support cable away from the intake (13). The flange bolts (4) joining the first and second stage are removed and the stages, separated. Once laid aside, the first stage hinges to the second by the cable connectors (19) of the first and second stages. The flowmeter (20) can easily be read at this time or removed by by unscrewing and extracting from the first stage, the threaded flowmeter support rod (21). The net (22) can be pulled from the inside of the second stage (2). and the plankton bucket (23), removed by releasing the retaining ring (24).

If the motor (25) should fail or the propeller (26) become damaged, the second stage and third stages can be separated in the same manner as the first and second. The motor is released by unscrewing the four motor bolts (27) which secure the motor to the motor struts (28). The flat motor struts also straighten the flow pattern created by the propeller (26) and, thusly, reduce any tendency of the collector to twist and to tangle the electric power and support cable (15).

What is claimed is:

1. A plankton collector for filtering plankton from water comprising: a hollow cylinder open at both ends providing an intake and outlet end, a motor driven propeller and a net mounted within said cylinder whereby plankton is filtered by said net upon rotation of said propeller; a closing means having a planar shape including a circular periphery and a diameter greater than the inside diameter of said intake end, said closing means including a hollow cylinder attached to a central hole in said closing means, said hollow cylinder attached to said closing means slidingly surrounds a tether, said tether being attached to said intake end and extending centrally therefrom such that upon completion of a collecting period, said closing means is slid along said tether thereby closing said intake end.

* * * * *